(12) United States Patent
Price et al.

(10) Patent No.: US 11,529,080 B2
(45) Date of Patent: Dec. 20, 2022

(54) BLOOD COLLECTION ASSEMBLY

(71) Applicant: The Monarch Company, LLC, Birmingham, AL (US)

(72) Inventors: James Price, Birrmingham, AL (US); Jonathan Trawick, Birmingham, AL (US); Clint Semmann, Waseca, MN (US)

(73) Assignee: THE MONARCH COMPANY LLC, Birmingham, AL (US)

( * ) Notice: Subject to any disclaimer, the term of this patent is extended or adjusted under 35 U.S.C. 154(b) by 750 days.

(21) Appl. No.: 16/390,499

(22) Filed: Apr. 22, 2019

(65) Prior Publication Data

US 2020/0330015 A1     Oct. 22, 2020

(51) Int. Cl.
*A61B 5/15*     (2006.01)
*A61B 5/153*    (2006.01)
*A61M 25/00*    (2006.01)
*A61M 25/06*    (2006.01)

(52) U.S. Cl.
CPC ........ *A61B 5/150641* (2013.01); *A61B 5/153* (2013.01); *A61B 5/15003* (2013.01); *A61B 5/15074* (2013.01); *A61B 5/150389* (2013.01); *A61M 25/0097* (2013.01); *A61M 25/0631* (2013.01); *A61M 25/0637* (2013.01)

(58) Field of Classification Search
CPC ........ A61B 5/150641; A61B 5/150389; A61B 5/15074; A61B 5/153; A61B 5/15003; A61B 5/150633; A61B 5/150648; A61B 5/150656; A61B 5/150664; A61B 5/15; A61B 5/150007; A61B 5/150015; A61B 5/150022; A61B 5/15019; A61B 5/150206; A61B 5/150251; A61B 5/150274–297; A61B 5/150351; A61B 5/150354; A61M 25/0097; A61M 25/0631; A61M 25/06–0637
USPC ....................................................... 600/576
See application file for complete search history.

(56) References Cited

U.S. PATENT DOCUMENTS 3,734,080 A * 5/1973 Petterson ......... A61B 5/150572
                                              600/577
4,676,783 A    6/1987 Jagger et al.
4,747,831 A    5/1988 Kulli
4,781,692 A   11/1988 Jagger et al.
(Continued)

FOREIGN PATENT DOCUMENTS

CA    2356199 A1 *  6/2000  ....... A61B 5/150656
CA    2384546 A1 *  4/2001
(Continued)

*Primary Examiner* — Matthew Kremer
*Assistant Examiner* — Om A. Patel
(74) *Attorney, Agent, or Firm* — Larkin Hoffman Daly & Lindgren, Ltd.

(57) ABSTRACT

The present disclosure is a blood collection assembly that has a needle assembly fixedly coupled to a finger-activated actuator and tubing and the needle assembly has a needle. Further, the blood collection assembly has a hub that houses the needle assembly and the hub has a channel in a top surface of the hub. Additionally, the channel slidably engages the finger-activated actuator such that when the finger-activated actuator is moved from a distal end of the hub to a proximal end of the hub the needle retracts within the hub.

19 Claims, 4 Drawing Sheets

(56) References Cited

U.S. PATENT DOCUMENTS

| | | | |
|---|---|---|---|
| 5,085,639 A * | 2/1992 | Ryan | A61M 5/3243 604/110 |
| 5,088,982 A | 2/1992 | Ryan | |
| 5,120,320 A | 6/1992 | Fayngold | |
| 5,176,655 A | 1/1993 | McCormick et al. | |
| 5,498,241 A | 3/1996 | Fabozzi | |
| 5,549,571 A | 8/1996 | Sak | |
| 5,573,512 A | 11/1996 | van den Haak | |
| 5,746,215 A | 5/1998 | Manjarrez | |
| 5,779,679 A | 7/1998 | Shaw | |
| 5,928,199 A | 7/1999 | Nakagami | |
| 5,951,525 A | 9/1999 | Thorne et al. | |
| 6,210,371 B1 | 4/2001 | Shaw | |
| 6,309,376 B1 | 10/2001 | Alesi | |
| 6,673,047 B2 | 1/2004 | Crawford et al. | |
| 6,743,186 B2 | 6/2004 | Crawford et al. | |
| 6,773,419 B2 | 8/2004 | Crawford et al. | |
| 6,835,190 B2 | 12/2004 | Nguyen | |
| 6,918,891 B2 | 7/2005 | Bressler et al. | |
| 7,018,344 B2 | 3/2006 | Bressler et al. | |
| 7,144,387 B2 | 12/2006 | Millerd | |
| 8,308,691 B2 * | 11/2012 | Woehr | A61M 39/22 604/167.01 |
| 8,469,927 B2 | 6/2013 | Shaw et al. | |
| D751,691 S | 3/2016 | Shaw et al. | |
| 2003/0181874 A1 | 9/2003 | Bressler et al. | |
| 2005/0119627 A1 | 6/2005 | Crawford | |
| 2013/0289524 A1 * | 10/2013 | Crawford | A61M 25/0631 604/506 |

FOREIGN PATENT DOCUMENTS

| | | | |
|---|---|---|---|
| CN | 1515329 A | * | 7/2004 |
| EP | 3024514 B1 | | 6/2017 |

* cited by examiner

BLOOD COLLECTION ASSEMBLY

BACKGROUND

Blood collection assemblies often comprise a small diameter needle having a pointed distal end and a proximal end mounted to a hub. Sometimes, the hub has wings mounted on either side. These wings may be used for a number of things. As an example, the wings may stabilize the blood collection assembly as the needle is inserted into a patient's arm.

Some blood collection assemblies have safety devices that protect users and patients from the needle after the needle has been used. For example, one blood collection assembly comprises a button that when selected actuates a spring drawing the needle into the hub. Another blood collection assembly comprises actuating wings, such that when the wings are rotated upward and together, a spring is initiated that retracts the needle. There are other types of safety devices on other blood collection assemblies.

Many of the existing safety devices are not put in place until the needle is removed from the person's arm. Thus, many existing safety devices still leave the needle exposed momentarily. This momentary exposure can lead to an accidental needle stick.

BRIEF DESCRIPTION OF THE DRAWINGS

The present disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure describes an exemplary blood collection assembly. The exemplary blood collection assembly comprises a hub that contains a needle assembly. In one embodiment, the hub comprises a set of wings that are used to balance the blood collection assembly as a needle is injected into a patient's arm.

Within a top side of the hub is a channel. Slidably coupled to the channel is a finger-activated actuator. The finger-activated actuator is situated toward the distal end of the hub when the needle is in an advanced position, such as when the needle is inserted into the patient's arm. When it is time to remove the needle from the patient's arm, a user slides the finger-activated actuator toward the proximal end of the hub until the needle is completely within the hub. Thus, the needle is removed from the patient's arm with little risk of accidental sticks.

In addition, at the distal end of the hub situated above the needle when the needle is in the advanced position is a compressed cotton and plastic shield. The compressed cotton and plastic shield is inside a compartment that is situated on a top side of the hub. When the needle is retracted by the finger-activated actuator, the compressed cotton and plastic shield falls down between the distal end of the needle and the needle opening in the hub. The cotton absorbs any excess liquid or blood and the plastic protects users from the distal end of the needle ensuring that the needle does not advance.

Figure 1:
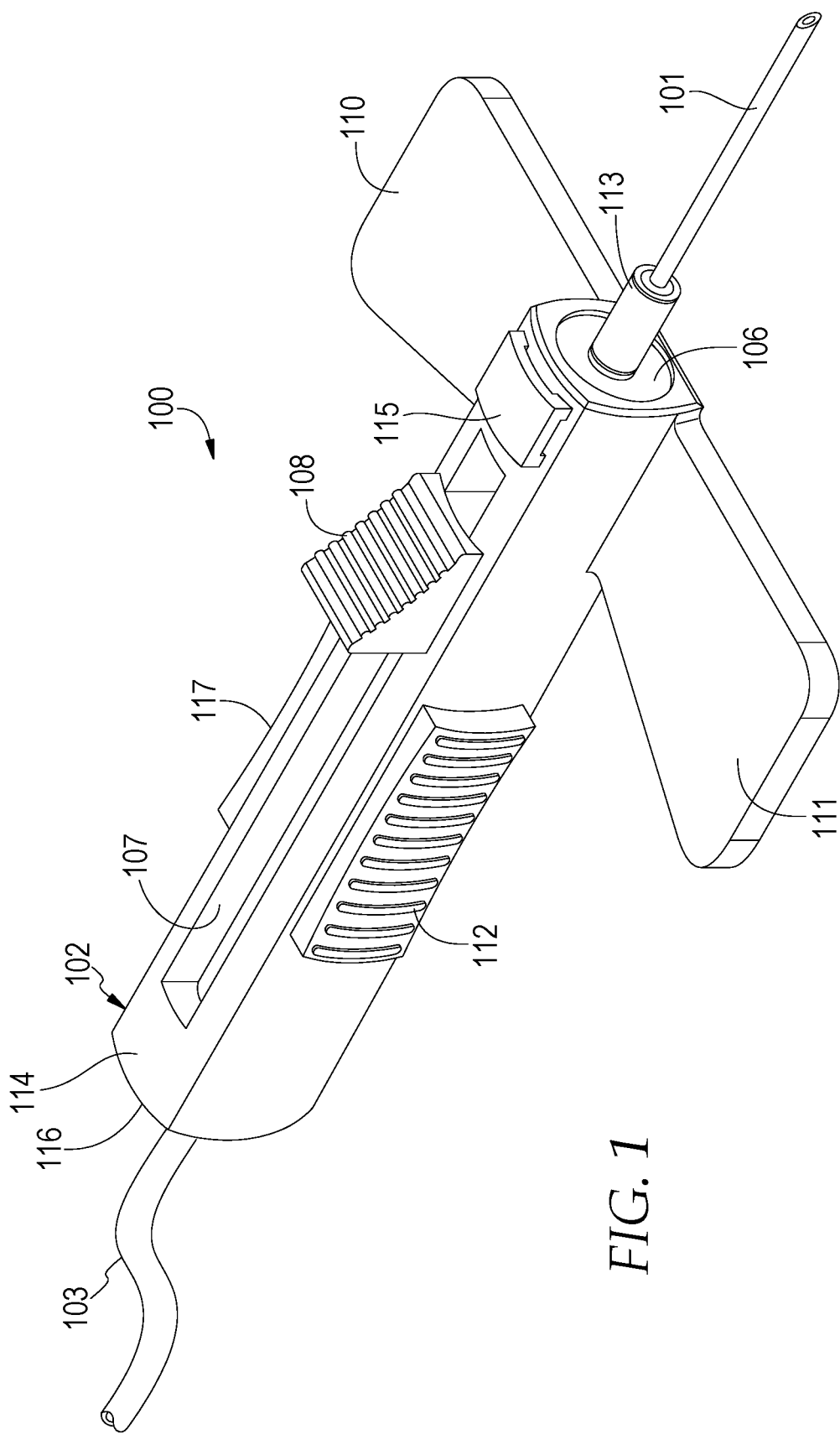
FIG. 1 is a perspective view of an exemplary blood collection assembly in accordance with an embodiment of the present disclosure with a needle advanced.

FIG. 1 is a perspective view of a blood collection assembly 100 in accordance with an embodiment of the present disclosure when a needle 101 is in an advanced position. An "advanced position" indicates that the needle is protruding for insertion into a patient's arm (not shown). The needle 101 protrudes from a plastic lid receptacle 113 to which a safety plastic lid (not shown) is coupled before use of the blood collection assembly 100.

The blood collection assembly 100 comprises a hub 102, a needle 101, and flexible tubing 103. In one embodiment, the flexible tubing 103 may comprise a clamp (not shown) for clamping the flexible tubing 103 to prohibit blood from fluidically travelling through the tubing. In use, the needle 101 is inserted in the patient's arm, blood flows through a needle assembly (not shown) that is coupled to the flexible tubing 103, and the blood flows through the flexible tubing 103 to a reservoir (not shown).

The blood collection assembly 100 further comprises a substantially cuboidal-shaped channel 107 formed in a top surface 114 of the hub 102. The substantially cuboidal-shaped channel 107 runs rectilinearly from a distal end 106 to a proximal end 116 of the hub 102. Slidably engaged with the cuboidal-shaped channel 107 is a finger-activated actuator 108, and the finger-activated actuator 108 is fixedly coupled to the needle assembly within the hub 102, which is described further herein.

In operation, a user inserts the needle 101 in a patient's arm. Blood is collected via the flexible tubing 103 in the reservoir. After the blood is collected, the user places his/her finger on the finger-activated actuator 108 and pulls the finger-activated actuator 108 to the proximal end 116 of the hub 102. Once the finger-activated actuator 108 has been moved to the proximal end 116 of the hub 102, the needle 101 is completely inside the hub 102. Thus, the needle 101 does not pose an accidental stick risk.

The blood collection assembly 100 further comprises wings 110 and 111. The wings 110 and 111 are coupled to and extend laterally from the distal end 106 of the hub 102. The wings 110 and 111 stabilize the blood collection assembly 100 while the needle 101 is inserted into the patient's arm. Further, the wings 110 and 111 stabilize the blood collection assembly 100 post insertion while blood is being drawn. Additionally, the wings 110 and 111 stabilize the assembly 100 when the finger-activated actuator 108 is actuated.

The blood collection assembly 100 further comprises a compartment 115. The compartment 115 houses a compressed cotton and plastic shield (not shown) that is housed in the hub 102. While the needle 101 is in the advanced position, the compressed cotton and plastic shield rests above the needle 101. However, when the needle 101 is moved to a retracted position via the finger-activated actuator 108, the compressed cotton and plastic shield falls between the distal end of the needle 101 and the plastic lid receptacle 113 inside the hub 102. The compressed cotton absorbs any fluid or blood that might leak from the needle 101 and the plastic shields the needle 101 from advancing through the plastic lid receptacle 113.

The blood collection assembly 100 further comprises gripper pads 112 and 117. The gripper pads 112 and 117 are coupled to or integral with the sides of the hub 102. The gripper pads 112 and 117 enable the user to easily grip the blood collection assembly 100 while in use. In this regard, the gripper pads 112 and 117 allow the user to easily grasp the blood collection assembly 100 when the user is collecting blood from the patient's arm or when the user is actuating the finger-activated actuator 108 to retract the needle 101.

Figure 2:
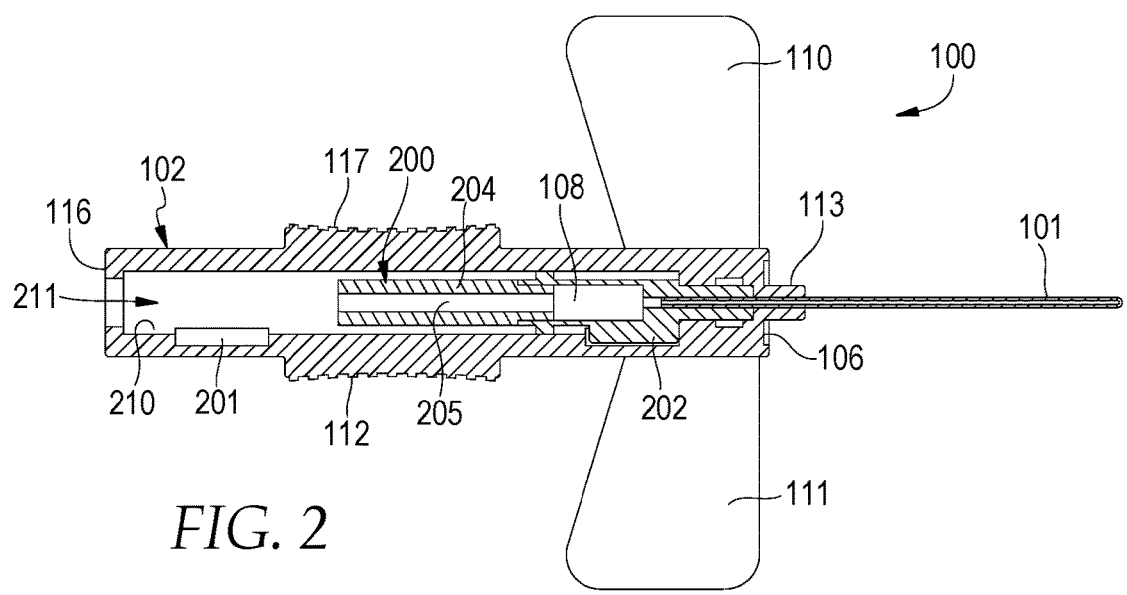
FIG. 2 is a top cross-sectional view of the blood collection assembly with the needle advanced as shown in FIG. 1.

FIG. 2 is a top cross-sectional view of the blood collection assembly 100 when the needle 101 is in the advanced position for insertion into a patient's arm. Note that prior to use of the blood collection assembly 100, a plastic lid (not shown) is coupled to the plastic lid receptacle 113 on the distal end of the hub 102 to protect from accidental sticks. In FIG. 2, the plastic lid is shown removed from the blood collection assembly 100, and the needle is exposed.

Note that the gripper pads 112 and 117 are shown coupled to or integral with the sides of the hub 102. As described hereinabove, the gripper pads 112 and 117 enable the user to easily grip the blood collection assembly 100 while in use.

Further note that the wings 110 and 111 are shown coupled to the distal end 106 of the hub 102. As described hereinabove, the wings 110 and 111 stabilize the blood collection assembly 100 while in use.

The blood collection assembly 100 further comprises a needle assembly 200. The needle assembly is moveably contained within a chamber 211 of the hub 102. The needle assembly 200 comprises a tubular member 204. The tubular member 204 comprises a cylindrical channel 204 defined by an inner wall 205. The needle assembly 200 is fixedly coupled to the needle 101 and the tubing 103 (FIG. 1). Additionally, the finger-activated actuator 108 is fixedly coupled to the needle assembly 200 such that when the finger-activated actuator 108 is moved from the distal end 106 to the proximal end 116 of the hub 102, the needle assembly 200 moves with the finger-activated actuator 108 from the distal end 106 to the proximal end 116 of the hub 102.

The needle assembly 200 further comprises a substantially rectangular-shaped protrusion 202. In operation, when the needle assembly 200 is moved via the finger-activated actuator 108 to the proximal end 116 of the hub 102, the rectangular-shaped protrusion 202 rests within a substantially rectangular-shaped indentation 201 in an inside surface 210 of the hub 102. In this regard, the rectangular-shaped protrusion 202 locks into the rectangular-shaped indentation 201 thereby fixing the needle assembly 200 at the proximal end of the hub 102. Thus, the needle assembly 200, including the needle 101, can no longer move toward the distal end 106 of the hub 102. Therefore, users are protected from the needle 101 when the needle assembly 200 is in the retracted position, which is shown with reference to FIG. 6.

Figure 3:
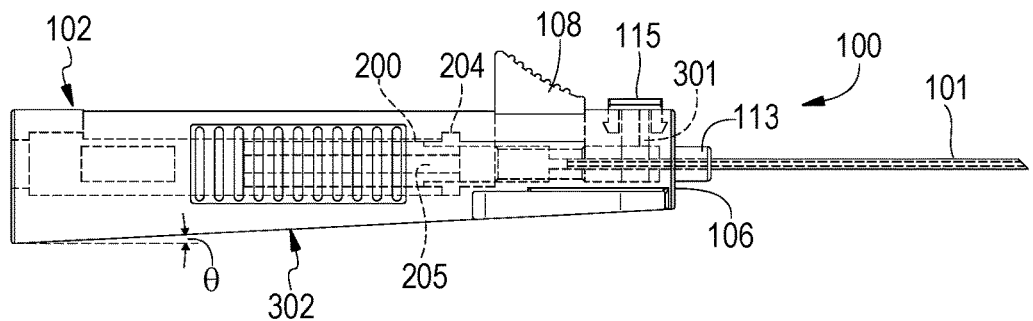
FIG. 3 is a side elevational view of the blood collection assembly with the needle advanced as shown in FIG. 1.

FIG. 3 is a side elevational view of the blood collection assembly 100 when the needle is in the advanced position. In this regard, the needle assembly 200 comprises the tubular member 204. The tubular member 204 comprises the cylindrical channel 204 defined by the inner wall 205. The needle assembly 200 comprises the needle 101 that is fixedly coupled to the tubular member 204. Additionally, the finger-activated actuator 108 is fixedly coupled to the needle assembly 200 such that when the finger-activated actuator 108 is moved from the distal end 106 to the proximal end 116 of the hub 102, the needle assembly 200 moves with the finger-activated actuator 108 to the proximal end 116 of the hub 102.

The blood collection assembly 100 further comprises a compressed cotton and plastic shield 301. The compressed cotton and plastic shield 301 is situated in the compartment 115 above the needle assembly 200 when the needle assembly 200 is in the advanced position. Note that as will be shown further herein, when the needle assembly 200 is retracted by the finger-activated actuator 108, the compressed cotton and plastic shield 301 falls downward resting between the distal end of the needle 101 and the receptacle 113. The compressed cotton of the shield 301 absorbs any excess liquid or blood from the needle 101, and the plastic portion of the shield 301 safely ensures that the needle 101 does not advance outwardly through the receptacle 113.

The blood collection assembly 100 further comprises an angled bottom surface 302. In one embodiment, the surface 302 is angled at an acute angle θ. When the blood collection assembly 100 is in use, the angled bottom surface 302 rests on the patient's arm thereby allowing the needle 101 to be more easily inserted. Further, the angle bottom surface 302 levels the blood collection assembly 100 so that when the finger-activated actuator 108 is moved by the user, the blood collection assembly 100 remains stabilized.

Figure 4:
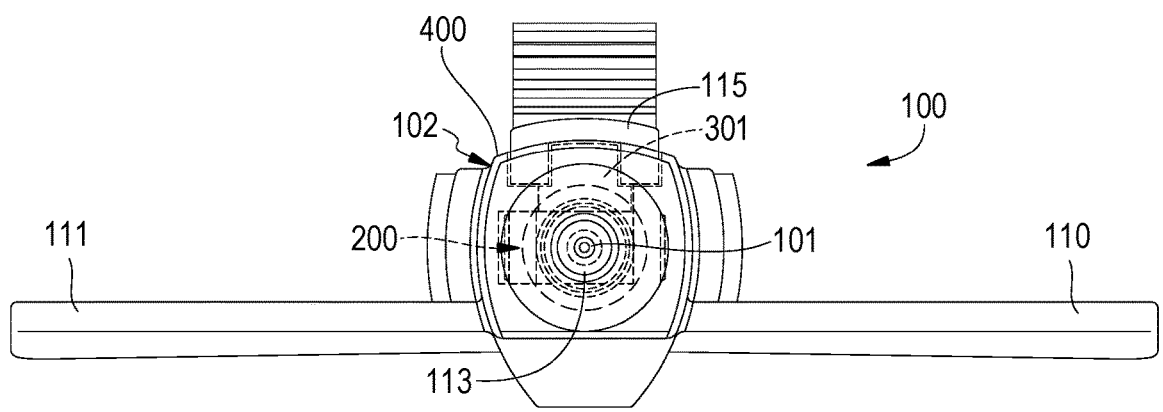
FIG. 4 is an end elevational view of the blood collection assembly with the needle advanced as shown in FIG. 1.

FIG. 4 is an end elevational view of the blood collection assembly 100 when the needle assembly 200 is in the advanced position and the needle 101 protrudes from the receptacle 113. Further, wings 110 and 111 protrude laterally from the hub 102 for stabilization of the blood collection assembly 100.

The blood collection assembly 100 comprises the compartment 115 that protrudes from an upper surface 400 of the hub 102. While the needle assembly 200 is in the advanced position, the compressed cotton and plastic shield 301 is situated within the compartment 115 above the needle 101. As will be shown further herein, when the needle assembly 200 is retracted, the compressed cotton and plastic shield 301 falls downward and rests between the distal end of the needle 101 and the receptacle 113.

Figure 5:
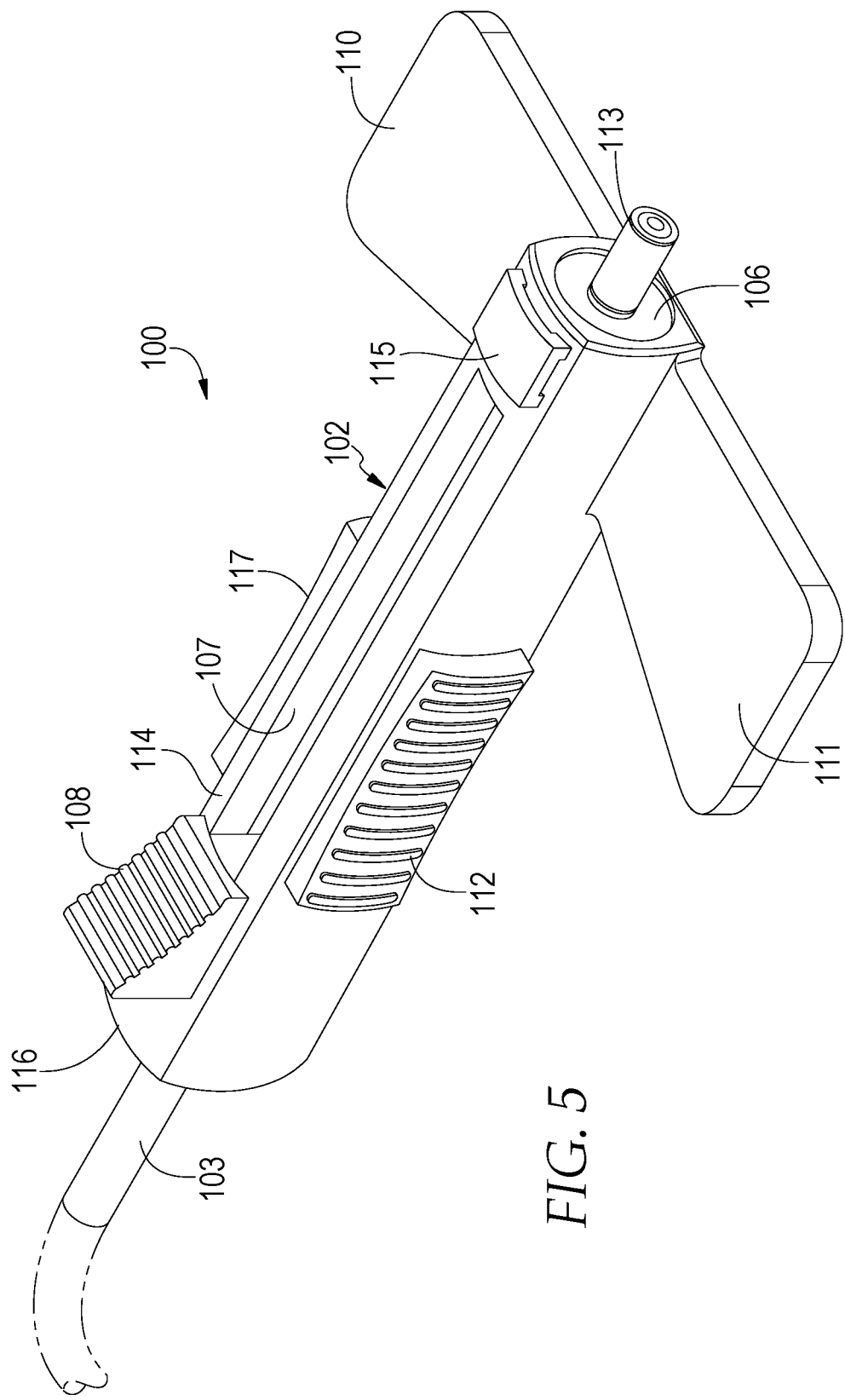
FIG. 5 is a perspective view of the blood collection assembly of FIG. 1 with the needle retracted.

FIG. 5 is a perspective view of the blood collection assembly 100 in accordance with an embodiment of the present disclosure when the needle 101 is in a retracted position. A "retracted position" indicates that the needle has been moved from the patient's arm and is housed within the hub 102. In this regard, the needle 101 no longer protrudes from the plastic lid receptacle 113.

As described hereinabove, the blood collection assembly 100 further comprises the substantially cuboidal-shaped channel 107 formed in the top surface 114 of the hub 102. The substantially cuboidal-shaped channel 107 runs rectilinearly from the distal end 106 to a proximal end 116 of the hub 102. Slidably engaged with the cuboidal-shaped channel 107 is the finger-activated actuator 108, and the finger-activated actuator 108 is fixedly coupled to the needle assembly 200 (FIG. 2) within the hub 102.

In operation, a user inserts the needle 101 in a patient's arm. Blood is collected via the flexible tubing 103 in the reservoir. After the blood is collected, the user places his/her finger on the finger-activated actuator 108 and pulls the finger-activated actuator 108 to the proximal end 116 of the hub 102. Once the finger-activated actuator 108 has been moved to the proximal end 116 of the hub 102, the needle 101 is completely inside the hub 102. Thus, the needle 101 no longer poses an accidental stick risk.

The blood collection assembly 100 further comprises the wings 110 and 111. As described hereinabove, the wings 110 and 111 are coupled to and extend laterally from the distal end 106 of the hub 102. The wings 110 and 111 stabilize the blood collection assembly 100 while the needle 101 is inserted into the patient's arm. Further, the wings 110 and 111 stabilize the blood collection assembly 100 post insertion while blood is being drawn.

The blood collection assembly 100 further comprises the compartment 115. The compartment 115 houses the compressed cotton and plastic shield 301 (FIG. 3) that is housed in the hub 102. While the needle 101 is in the advanced position, the compressed cotton and plastic shield 301 rests above the needle 101. However, when the needle 101 is moved to the retracted position via the finger-activated actuator 108, the compressed cotton and plastic shield 301 falls downwardly between the distal end of the needle 101 and the plastic lid receptacle 113 inside the hub 102. The compressed cotton absorbs any fluid or blood that might leak from the needle 101, and the plastic shields the needle 101 from advancing through the plastic lid receptacle 113.

As described hereinabove, the blood collection assembly 100 further comprises the gripper pads 112 and 117. The gripper pads 112 and 117 are coupled to or integral with the sides of the hub 102. The gripper pads 112 and 117 enable the user to easily grip the blood collection assembly 100 while in use.

Figure 6:
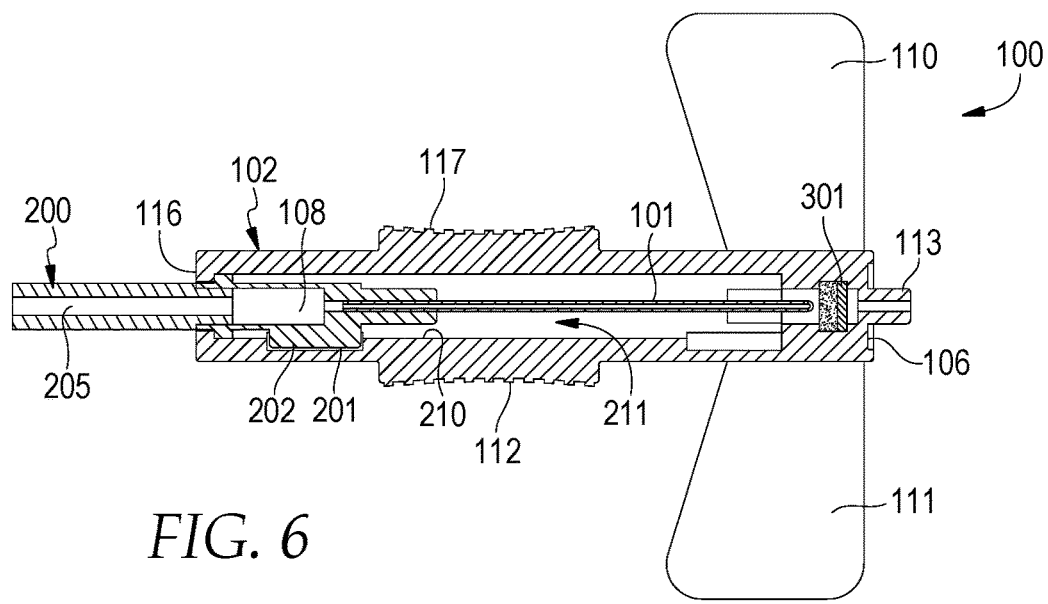
FIG. 6 is a top cross-sectional view of the blood collection assembly as shown in FIG. 1 with the needle retracted.

FIG. 6 is a top cross-sectional view of the blood collection assembly 100 when the needle 101 is in the retracted position. Note that prior to use of the blood collection assembly 100, a plastic lid (not shown) is coupled to the plastic lid receptacle 113 on the distal end of the hub 102 to protect from accidental sticks. In FIG. 6, the plastic lid is shown removed from the blood collection assembly 100, and the needle is retracted.

Note that the gripper pads 112 and 117 are shown coupled to or integral with the sides of the hub 102. As described hereinabove, the gripper pads 112 and 117 enable the user to easily grip the blood collection assembly 100 while in use.

Further note that the wings 110 and 111 are shown coupled to the distal end 106 of the hub 102. As described hereinabove, the wings 110 and 111 stabilize the blood collection assembly 100 while in use.

The blood collection assembly 100 further comprises the needle assembly 200. The needle assembly 200 is moveably contained within the chamber 211 of the hub 102. The needle assembly 200 comprises the tubular member 204. The tubular member 204 comprises the cylindrical channel 204 defined by the inner wall 205. The needle assembly 200 is fixedly coupled to the needle 101 and the tubing 103 (FIG. 5). Additionally, the finger-activated actuator 108 is fixedly coupled to the needle assembly 200 such that when the finger-activated actuator 108 is moved from the distal end 106 to the proximal end 116 of the hub 102, the needle assembly 200 moves with the finger-activated actuator 108.

The needle assembly 200 further comprises the substantially rectangular-shaped protrusion 202. In operation, when the needle assembly 200 is moved via the finger-activated actuator 108 to the proximal end of the hub 102, the rectangular-shaped protrusion 202 rests within the substantially rectangular-shaped indentation 201 within an inside surface 210 of the hub 102. In this regard, the rectangular-shaped protrusion 202 locks into the rectangular-shaped indentation 201 thereby fixing the needle assembly 200 at the proximal end of the hub 102. Thus, the needle assembly 200, including the needle 101, can no longer move toward the distal end 106 of the hub 102. Therefore, users are protected from the needle 101 when the needle assembly 200 is in the retracted position.

Further, when the needle assembly 200 is moved to the proximal end 116 of the hub 102, the compressed cotton and plastic shield 301 falls downwardly. The compressed cotton and plastic shield 301 rests between the distal end of the needle 101 and the receptacle 113. Thus, the compressed cotton portion of the shield absorbs any fluid or blood that escapes the needle 101. The plastic portion of the shield 301 safely ensures that the needle 101 does not advance outwardly through the receptacle 113 posing an accidental stick risk.

Figure 7:
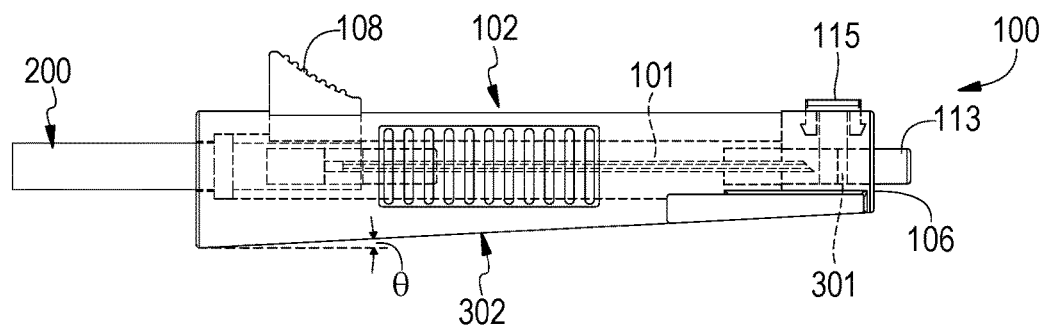
FIG. 7 is a side elevational view of the blood collection assembly as shown in FIG. 1 with the needle retracted.

FIG. 7 is a side elevational view of the blood collection assembly 100 when the needle is in the retracted position. In this regard, the needle assembly 200 comprises the needle 101. Additionally, the finger-activated actuator 108 is fixedly coupled to the needle assembly 200 such that when the finger-activated actuator 108 is moved from the distal end 106 to the proximal end 116 of the hub 102, the needle assembly 200 moves with the finger-activated actuator 108.

The blood collection assembly 100 further comprises the compressed cotton and plastic shield 301. When in the retracted position, the compressed cotton and plastic shield 301 is situated between the distal end of the needle 101 and the receptacle 113. The compressed cotton of the shield 301 absorbs any excess liquid or blood from the needle 101, and the plastic portion of the shield 301 safely ensures that the needle 101 does not advance outwardly through the receptacle 113.

The blood collection assembly 100 further comprises the angled bottom surface 302. In one embodiment, the surface 302 is angled at an acute angle θ. When the blood collection assembly 100 is in use, the angled bottom surface 302 rests on the patient's arm thereby allowing the needle 101 to be more easily inserted. Further, the angle bottom surface 302 levels the blood collection assembly 100 so that when the finger-activated actuator 108 is moved by the user, the blood collection assembly 100 remains stabilized.

Figure 8:
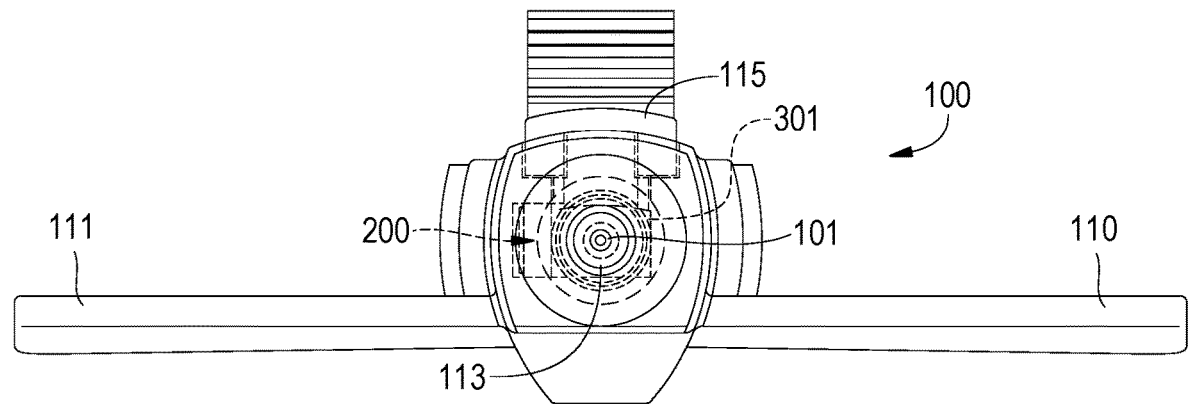
FIG. 8 is an end elevational view of the blood collection assembly as shown in FIG. 1 with the needle retracted.

FIG. 8 is an end elevational view of the blood collection assembly 100 when the needle assembly 200 is in the retracted position and the needle 101 (FIG. 6) is within the hub 102.

The blood collection assembly 100 comprises the compartment 115 that protrudes from an upper surface 400 of the hub 102 and houses the compressed cotton and plastic shield 301. When the needle assembly 200 is moved to the retracted position, the compressed cotton and plastic shield 301 falls downward and rests between the distal end of the needle 101 and the receptacle 113.

What We claim is:

1. A blood collection assembly, comprising:
a needle assembly fixedly coupled to a finger-activated actuator and tubing, the needle assembly comprising a needle; and
a hub configured for housing the needle assembly, the hub comprising a proximal end, a distal end, a channel and the compartment, the channel and compartment positioned in a spaced-apart relationship on a top side of the hub with the compartment positioned distal the channel, the hub further including at least two wings extending from a bottom side of the hub, the compartment housing a shield positioned above the needle, the channel slidably engaging the finger-activated actuator such that when the finger-activated actuator is moved along the channel from the distal end of the hub to the proximal end of the hub, the needle retracts within the hub and the shield falls toward the at least two wings between an end of the needle and the distal end of the hub.

2. The blood collection assembly of claim 1, further comprising at least two gripper pads, the at least two gripper pads coupled to or integral with opposed sides of the hub, the at least two gripper pads enable a user to easily grip the blood collection assembly while in use.

3. The blood collection assembly of claim 1, further comprising a safety top receptacle mounted to the distal end of the hub.

4. The blood collection assembly of claim 1, wherein the needle assembly further comprises a protrusion.

5. The blood collection assembly of claim 4, wherein the hub further comprises an indentation on an inside surface of the hub.

6. The blood collection assembly of claim 5, wherein the blood collection assembly is configured such that when the needle assembly is moved to a retracted position, the protrusion locks into the indentation thereby locking the needle assembly at the proximal end of the hub.

7. The blood collection assembly of claim 1, wherein the shield comprises a compressed cotton portion and a plastic portion.

8. The blood collection assembly of claim 7, wherein the compressed cotton portion is configured to absorb fluid or blood from the end of the needle.

9. The blood collection assembly of claim 8, wherein the plastic portion is configured to safely ensure that the needle does not advance outwardly through a lid receptacle positioned at the distal end of the hub.

10. The blood collection assembly of claim 1, wherein the hub has an angled bottom surface for stabilizing the hub for post insertion, for blood collection, and for needle retraction.

11. The blood collection assembly of claim 1, wherein the finger-activated actuator includes a forward surface angled away from the at least two wings.

12. The blood collection assembly of claim 1, wherein the needle assembly is movably contained within a chamber of the hub, and further wherein, upon retraction of the needle within the hub, the shield is configured to fall from the compartment to the chamber.

13. The blood collection assembly of claim 1, wherein the channel terminates at a proximal surface, the proximal surface facing toward the finger-activated actuator and away from the compartment.

14. A blood collection assembly, comprising:
a hub comprising a channel in a top surface, a finger-activated actuator slidably engaging the channel, the hub comprising a proximal end, a distal end and a channel in a top side of the hub, the hub further including at least two wings extending from a bottom side of the hub and a compartment on the top side of the hub at the distal end and spaced apart from the channel, the compartment positioned distal the channel, the compartment housing a shield, the channel slidably engaging the finger-activated actuator; and
a needle assembly comprising a needle, the needle assembly contained within a chamber of the hub and positioned below the shield, the needle assembly fixedly coupled to the finger-activated actuator such that when a user moves the finger-activated actuator from the distal end to the proximal end of the hub in the channel, the needle retracts within the hub and the shield falls toward the at least two wings between an end of the needle and the distal end of the hub.

15. The blood collection assembly of claim 14, wherein the needle assembly further comprises a protrusion, and the hub further comprises an indentation on an inside surface of the hub.

16. The blood collection assembly of claim 15, wherein the blood collection assembly is configured such that when the needle assembly is moved to a retracted position, the protrusion locks into the indentation thereby locking the needle assembly at the proximal end of the hub.

17. The blood collection assembly of claim 14, wherein the hub has an angled bottom surface for stabilizing the hub for post insertion, for blood collection, and for needle retraction.

18. The blood collection assembly of claim 14, wherein the finger-activated actuator includes a forward surface angled away from the at least two wings.

19. A method of blood collection, comprising:
accessing a hub comprising a channel in a top surface and a finger-activated actuator slidably engaging the channel, the hub comprising a proximal end, a distal end and a channel in a top side of the hub, the hub further including at least two wings extending from a bottom side of the hub and a compartment on the top side of the hub at the distal end and spaced apart from the channel, the compartment positioned distal the channel and housing a shield, the channel slidably engaging the finger-activated actuator; and
retracting a needle assembly comprising a needle, the needle assembly contained within a chamber of the hub and positioned below the shield, the needle assembly fixedly coupled to the finger-activated actuator such that when a user moves the finger-activated actuator from a distal end to a proximal end of the hub in the channel, the needle is positioned within the hub and the shield falls toward the at least two wings between an end of the needle and the distal end of the hub.

* * * * *

UNITED STATES PATENT AND TRADEMARK OFFICE
CERTIFICATE OF CORRECTION

PATENT NO. : 11,529,080 B2
APPLICATION NO. : 16/390499
DATED : December 20, 2022
INVENTOR(S) : James Price, Jonathan Trawick and Clint Semmann It is certified that error appears in the above-identified patent and that said Letters Patent is hereby corrected as shown below:

On the Title Page

Inventors, Line 1, delete "Birrmingham" and insert -- Birmingham --.

In the Claims

In Claim 6, Line 19, delete "thatwhen" and insert -- that when --.

In Claim 19, Line 48, delete "a distal end to a proximal" and insert -- the distal end to the proximal --.

Signed and Sealed this
Fourteenth Day of February, 2023

Katherine Kelly Vidal
*Director of the United States Patent and Trademark Office*